United States Patent [19]

Kelemen et al.

[11] Patent Number: 4,657,859

[45] Date of Patent: Apr. 14, 1987

[54] PROCESS FOR THE TREATMENT OF FERMENTATION BROTH CONTAINING VITAMIN $B_{12}$ AND OTHER CORRINOIDS AND FOR THE PREPARATION OF VITAMIN $B_{12}$ CONCENTRATES

[76] Inventors: Ágnes Kelemen, VII. Virányos ut 21a.; István Jaksa, XVI. Ságvári Endre ut 9.; Béla Stefkó, XII. Orlay ut 2b.; Eva Udvardy Nagy nee Cserey Pechany, XII. Böszörményi ut 40., all of Budapest, Hungary

[21] Appl. No.: 577,189

[22] Filed: Feb. 6, 1984

[30] Foreign Application Priority Data

Feb. 11, 1983 [HU] Hungary ............................. 469/83

[51] Int. Cl.⁴ ..................... C12P 19/42; A23K 1/16; A23L 1/302; B01D 15/00
[52] U.S. Cl. ..................................... 435/86; 435/803; 426/2; 426/72; 210/663
[58] Field of Search ............... 435/86, 803; 426/72, 426/2, 490; 210/663, 692; 514/81

[56] References Cited

U.S. PATENT DOCUMENTS

| | | |
|---|---|---|
| 3,085,049 | 4/1963 | Rudy et al. ............................ 435/86 |
| 3,169,100 | 2/1965 | Weinstein ............................. 435/86 |
| 3,531,463 | 9/1970 | Gustafson ............................ 210/692 |
| 4,144,373 | 3/1979 | Weiss et al. .......................... 428/306 |
| 4,145,304 | 3/1979 | Melnick et al. ....................... 435/30 |
| 4,383,110 | 5/1983 | Kinoshita et al. .................... 536/28 |
| 4,399,274 | 8/1983 | Goegelman et al. ................ 210/692 |
| 4,407,947 | 10/1983 | Koppenhagen et al. ............ 435/86 |
| 4,544,633 | 10/1985 | Kojima et al. ........................ 435/86 |
| 4,582,799 | 4/1986 | Jarvis .................................... 435/68 |
| 4,599,309 | 7/1986 | Ohsumi et al. ....................... 435/68 |

*Primary Examiner*—Thomas G. Wiseman
*Assistant Examiner*—Elizabeth C. Weimar
*Attorney, Agent, or Firm*—Karl F. Ross; Herbert Dubno

[57] ABSTRACT

A process is disclosed for the treatment of fermentation broths containing vitamin $B_{12}$ and other corrinoids, and for the preparation of vitamin $B_{12}$ concentrates or crystalline vitamin $B_{12}$ wherein the fermentation broth is contacted with a nonionic, macroreticular, adsorption resin having a pore size of $10^{-8}$ to $10^{-7}$ meters, a grain diameter of at least $10^{-4}$ m, and a specific surface area of at least 200 $m^2/g$ so that the macromolecular adsorption resin adsorbs fermentation broth additives and metabolites of fermentation, whereas the intact microorganism cells containing the vitamin $B_{12}$ remain in solution. The solution of intact vitamin $B_{12}$-containing cells is then treated further to obtain vitamin $B_{12}$ in still purer form.

10 Claims, No Drawings

PROCESS FOR THE TREATMENT OF FERMENTATION BROTH CONTAINING VITAMIN $B_{12}$ AND OTHER CORRINOIDS AND FOR THE PREPARATION OF VITAMIN $B_{12}$ CONCENTRATES

FIELD OF THE INVENTION

The invention relates to a process for the treatment of fermentation broth containing vitamin $B_{12}$ and other corrinoids and for the preparation of vitamin $B_{12}$ concentrates. More particularly, the invention concerns a process of high yield by which vitamin $B_{12}$ and other biologically active corrinoids or concentrates thereof can be isolated from a fermentation broth.

BACKGROUND OF THE INVENTION

During the microbiological preparation of vitamin $B_{12}$ and other corrinoids, vitamin $B_{12}$ produced by microorganisms is accumulated substantially intracellularly, and therefore is generally isolated from the fermentation broth by isolating the cell mass, e.g. by filtration, sedimentation and/or centrifugation, and disrupting the cells in the so called cell-cream (bio-mass) obtained (which can be utilized, after drying, also directly, as a vitamin $B_{12}$-containing fodder additive). Vitamin $B_{12}$ and the accompanying corrinoids are contained in a liquid phase from which they can be isolated by extraction or adsorption methods, after eliminating the cell debris and other solid impurities by filtration and/or centrifugation and optionally further purification or enrichment.

The known processes for the microbiological production of vitamin $B_{12}$ and for its isolation from the fermentation broth are for example disclosed in "Vitamin $B_{12}$ and verwandte Corrinoide" (R. Ammon: Fermente-Hormone-Vitamine, III/2, G. Thieme Verlag, Stuttgart, 1975, 10-13).

According to the known processes the separation of the microorganisms containing the corrinoids from the fermentation broth has technical difficulties and often cannot be carried out with a satisfactory yield. A further problem is that the fermentation broth contains vitamin $B_{12}$ in a relatively low concentration, accompanied with a large amount of partly suspended, partly dissolved impurities; hence it is very difficult to find a technically suitable and economic method for the isolation of the active ingredient from its low level solution obtained after the disruption of the cells. These difficulties are particularly serious when the fermentation medium is inoculated with sludge (e.g. methane-forming septic fermentations), since in these cases the corrinoids produced must be separated from considerably more accompanying impurities, which are more difficult to eliminate than in case of sterile fermentation, for example with Propionibacteria.

There have been numerous attempts to eliminate the above difficulties, using various additional purification or enrichment steps to facilitate the isolation of vitamin $B_{12}$ in high purity.

According to the Hungarian Patent Specification No. 158,809 the cells are separated from the fermentation broth of *Propionibacterium shermanii;* they are disrupted and the pH of the medium is gradually adjusted to 5.5–6.5. Under such conditions a part of the impurities, especially the proteins are bound to the biomass, while vitamin $B_{12}$ remains in the solution. The biomass and the accompanying impurities are then separated by centrifugation or sedimentation and vitamin $B_{12}$ and other corrinoids are isolated from the purified solution by ion exchange. This process is difficult to carry out on an industrial scale since the separation of the cell debris and the precipitated impurities is cumbersome, and the use of filtration-sedimentation aids may lead to a substantial loss in active ingredient.

According to the Soviet Patent Specification No. 161,709 the complete fermentation broth or the separated biomass is treated by heat in an acidic medium, the solid particles are separated by centrifuging, and the active ingredient is adsorbed from the supernatant by alumina or an ion exchange resin. The micron-size cells and other fine, suspended impurities can, however, not be isolated completely by centrifugation, and in the presence of the residual impurities the effectivity of the adsorption isolation of active ingredient is not satisfactory, and the practical performance of the process is often hindered by serious technical difficulties.

The isolation of certain active ingredients from their fermentation broths containing cells or cell debris and other solid impurities has considerably been facilitated by the application of so called macroreticular adsorption resins. These hard, insoluble, porous, apolar or to a certain degree polar bead polymers having a large specific surface area due to their favorable pore size, grain size and mechanical stability allow even the adsorption of materials dissolved in mixtures containing solid particles, for example by fluidized bed or batchwise operation. Thus the cumbersome filtration or centrifugation of the fermentation broth can be avoided and the whole amount of the fermentation broth can be introduced into the adsorption system. A disadvantage of this method is that in addition to the active ingredient a considerable amount of impurities is adsorbed on the resin. Processes based on the principle described above can be employed also when the corrinoids are the active ingredients in the fermentation medium, since it is known (U.S. Pat. No. 3,531,463) that some macroreticular adsorption resins adsorb corrinoids from their aqueous solutions, and the corrinoids can be eluted from these resins with suitable solvents. However, until now there has been no process known in the art for the adsorption of corrinoids from fermentation broths, which, in addition to the elimination of the disadvantages of other known processes, could have been carried out easily and could have provided the active ingredient in satisfactory purity and with a good yield.

DESCRIPTION OF THE INVENTION

We have found that the corrinoids produced by microorganisms, which are present in the fermentation broth intracellularly, can be recovered with a good yield and in a high purity by a two-step method, in which the adsorbent does not suffer any damage.

In the first step of the process the native fermentation broth obtained at the end of the fermentation, is treated with a macroporous, so called macroreticular adsorption resin of high specific surface area, at room temperature, without any pre-treatment. Under such conditions the macroreticular resin adsorbs some additives of the fermentation broth and some unspecific metabolites of fermentation, whereas the intact cells together with the corrinoids contained therein remain in the fermentation fluid.

In the purified fermentation fluid the cells are then disrupted in a known manner, e.g. by heat treatment in the presence of cyanide ions. As a result, the corrinoids are released into solution, while the debris of the disrupted cells remain suspended in the liquid, which is treated in a second adsorption step again with a macroreticular adsorption resin, directly, without elimination of the cell debris and other solid impurities. In this step the active ingredient is adsorbed on the resin. Since during the disruption of the cells unavoidably also soluble impurities are dissolved in the fermentation medium, these are also adsorbed on the resin in the second adsorption step to certain extent. The majority of these impurities can, however, be separated from the adsorbed corrinoids selectively, with an alkaline-aqueous treatment of the resin, and therefore do not contaminate the desired end product. The corrinoids remain on the surface of the resin during this operation. When the fermentation media are less contaminated, and for example are obtained in an aseptic fermentation, such impurities soluble in an alkaline-aqueous medium are not necessarily adsorbed on the resin in the second adsorption step. If this is the case, the alkaline-aqueous treatment of the resin carrying the adsorbed corrinoids can be omitted, since the solid impurities can be washed off with pure water, and the corrinoids can then be eluted from the resin in a good purity.

The desired corrinoids are then eluted from the absorbent treated as described above, in a known manner, with an organic solvent, e.g. a lower alcohol or ketone, optionally containing water. The eluate can be used for a vitamin $B_{12}$ fodder additive in a known manner or alternatively, for the isolation of crystalline vitamin $B_{12}$ or other corrinoids according to known processes.

In the two adsorption steps of the process according to the invention any known macroreticular (pore size: $10^{-8}$ to $10^{-7}$ m., grain size: at least $10^{-4}$ m., specific surface area: at least 200 m.$^2$/g.), non-ionic adsorption resin, e.g. Amberlite XAD-2, XAD-4, XAD-7, XAD-8 or XAD-9 (products of Rohm and Haas, U.S.A.), or DIAION HP-20, HP-21, HP-2 mG (Mitsubishi, Japan) can be employed with good results. The adsorption resins used in the two subsequent adsorption steps can be identical or different; if different resins are employed, the difference may reside for example in the pore size or the polarity of the surface. The optimum resin should be selected depending on the type of the fermentation medium and the character of the impurities present, experimentally. It may prove to be advantageous to treat the native fermentation broth with two different resins, e.g. having a smaller and a larger pore size, or non-ionic apolar and non-ionic but more or less polar character, respectively, in the first adsorption step. The further conditions of the adsorption steps which are generally performed at room temperature, e.g. the optimum pH-value and the optimum contact time with the resin, may also vary depending on the quality of the given fermentation medium and on its actual composition, therefore, the most preferred conditions should be determined experimentally.

When treating the fermentation broth containing intact cells with an adsorption resin, the operation conditions must not be damaging to the cells, e.g. strongly acidic (pH<5) or alkaline (pH>8) conditions and high temperatures should be avoided. In the first adsorption step, if carried out under optimally selected conditions, a purified fermentation broth should be obtained, which is essentially devoid of any colored impurity or impurities of unpleasant odor, and contains only a minimum amount of lipoids. In the tentative experiments the presence of colored impurities or components of unpleasant odor can be controlled by organoleptic examinations, while the lipoid content can be determined by extraction with a fat-extraction solvent and determination of the fat concentration of the extract.

The technical realization of adsorption may vary depending on the equipment chosen. Thus, in a batchwise operation the resin can be admixed with the fermentation broth, and can be separated carrying the adsorbed materials, with conventional techniques, e.g. sedimentation, filtration. According to another preferred embodiment, the adsorption can be performed with a fluidized bed technique.

In the second adsorption step, which takes place after the disruption of the cells, the impurities adsorbed on the resin-together with the active ingredient-can be eliminated selectively, using an akaline washing liquor for example a dilute aqueous ammonium hydroxide solution of pH 8-12, preferably pH 9-10. Other aqueous alkaline solutions, e.g. aqueous potassium or sodium hydroxide solution are equally suitable.

The active ingredient can be eluted from the resin in a known manner, for example with methanol or aqueous methanol.

The crude product obtained according to the invention by elution of the active material from the adsorption resin-which has first been subjected to an alkaline-aqueous washing-, and by subsequent evaporation of the eluate to dryness, is a water-soluble concentrate, which contains vitamin $B_{12}$ and other corrinoids in a high purity. Its biologically active corrinoid content (active ingredient content) is between 10 and 25% related to the dry substance content. This crude product in a dry state can directly be used as a vitamin $B_{12}$ fodder additive, on the other hand, due to its high purity and high corrinoid concentration, it is an excellent starting substance for the isolation of crystalline vitamin $B_{12}$ and of the so called factor III (5-hydroxybenzimidazolcobalamine).

Since the properties of the orginal fermentation broth which would be disadvantageous as to the application of the product obtained therefrom directly for feeding animals, such as unpleasant odor and taste are eliminated during the first adsorption treatment of the native fermentation broth, the purified fermentation broth obtained after the first adsorption step can be concentrated or evaporated to dryness to yield a vitamin $B_{12}$ fodder additive. As a result of pre-treatment, the specific weight of the fermentation broth is decreased, accordingly the separation of the microorganisms becomes easier. By this technology a light colored product is obtained, which is devoid of umpleasant odor.

The advantages of the process according to the invention can be summarized as follows:

(1) The performance of the two adsorption steps of the process and the disruption of the cells throughout in the original fermentation medium is very advantageous, since the solid parts of the fluid need not be separated during the procedures.

(2) In the first adsorption step carried out with the native broth with intact cells, the overwhelming part of the extracellular impurities will be adsorbed on the first adsorbent separately from the active ingredient, therefore the active ingredient can be adsorbed on an essentially smaller amount of adsorbent in the second step.

(3) As a result of the above-described technological changes the elution of the active ingredient can be carried out with a considerably lower amount of eluent, accordingly, the active ingredient concentration of the solution obtained will be much higher.

(4) The pre-treatment in the first adsorption step and the selective elution of the impurities by alkaline-aqueous treatment in the second adsorption steps substantially improve the purity of the eluted active ingredient. As a result, by the process according to the invention products containing 10% or more of active ingredient can be prepared without any additional purification or concentration.

(5) The process is easy to carry out even on an industrial scale. Most advantageously it can be carried out with the so called fluidized bed technology, which makes continuous operation possible.

(6) The use of the first adsorption step to diminish the extracellular impurities results in a purified broth having a better quality for subsequent operations, e.g. direct drying to feed additive or conventional extraction for crystalline vitamin $B_{12}$.

SPECIFIC EXAMPLES

Further details of the invention will now be illustrated by the following non-limiting Examples.

Example 1

2 m$^3$. of a fermentation broth obtained by anaerobic fermentation with a mixed bacterium population derived from sludge, having a dry substance content of 1.5% and a pH of 6.3, which contains 26 mg. of vitamin $B_{12}$ and 4.2 mg. of factor III (5-hydroxy-benzimidazol-cobalamine) per liter are purified in a two-member, fluidized bed adsorption system connected in series. The unfiltered fermentation medium is continuously passed upflow through two 50 liter units filled with 10 liter of DIAION HP 20 macroreticular adsorption resin (Mitsubishi, Japan) each, at a rate of 200 liter/hour. During this step a substantial amount of the extracellular impurities present in the fermentation medium is adsorbed on the resin. When the fermentation medium has been passed through, the equipment is washed with 100 liter of water.

To the partially purified fermentation medium 250 ml. of a 1% aqueous KCN solution are added, and the pH is then adjusted to 4 by continuous addition of a 50% aqueous sulfuric acid solution. Thereafter, the fermentation medium is heated up to 110° C. in a continuous system, with a contacting time of 10 minutes. In this step the cells are disrupted and the corrinoids set free from the cells are dissolved in the fermentation medium.

The fermentation medium is cooled to a temperature below 30° C. in a heat exchange system, and is then introduced into a second two-member adsorption system, in which the members each have a useful volume of 50 liter and are filled with 20 liter of a DIAION HP 20 macroreticular adsorption resin. The members of the fluidized bed adsorption system are connected in series, and the flow rate of the fermentation medium is 200 liter/hour. In this step corrinoids are adsorbed on the resin, the liquor passed through the equipment, without notable corrinoid content is discharged. Thereafter, 250 liters of water are passed upflow through the adsorption equipment at a rate of 1 m.$^3$/hour, in an opposite direction, to eliminate the digested cell residues remaining in the equipment. 200 liters of water the pH of which has been adjusted to 9 to 10 with ammonium hydroxide are then passed through the equipment. This aqueous alkaline solution eliminates the lipoids and not identified yellow and brown impurities from the adsorbent on which the corrinoids are adsorbed. The resin treated with the alkaline solution is washed to neutral, and the corrinoids are then eluted with 200 liters of methanol, introduced at a rate of 100 liters/hour. Methanol is eliminated from the eluate by vacuum evaporation at a temperature not exceeding 50° C. to yield 10 liters of an aqueous solution, which contains 45.2 g. of vitamin $B_{12}$ and 7.3 g. of factor III, and has a total dry substance content of 331 g. Accordingly, the specific active ingredient concentration related to the dry substance is 15.9%. It can be seen that the obtained concentrate contains the active ingredient in a 200-times higher concentration than the starting fermentation medium, the purification related to the dry substance is 92-fold, the yield of active ingredient related to the active ingredient concentration of the starting fermentation medium amounts to 87%.

The dry product obtained by spray-drying of the aqueous concentrate prepared as described above, can directly be used as a fodder additive having a higher vitamin $B_{12}$ concentration; and by extraction and further purification by ion exchange, can be converted into crystalline vitamin $B_{12}$ in a known manner.

Example 2

Into 100 liters of a fermentation broth obtained by an aseptic fermentation carried out with Propioni-bacterium shermanii, which contains 45 mg./liter of vitamin $B_{12}$ and 1.35% of dry substance, and has a pH of 5.9, 2 liters of Amberlite XAD 2 macroreticular resin are admixed. After stirring slowly for one hour the resin is eliminated by filtration through a filter which allows the microorganisms present in the fermentation broth to pass through. The purified fermentation medium obtained as a filtrate is then digested in a known manner, in the presence of cyanide ions, after adjusting the pH to 5.

The pH of the fermentation broth, after cooling to 30° C., is adjusted to 5–5.5, and 5 liters of Amberlite XAD 2 are added. During a three-hour stirring the total amount of vitamin $B_{12}$ present in the solution is adsorbed on the resin. The resin is eliminated by filtration, washed with water and vitamin $B_{12}$ is eluted from the resin by admixing with 10 liters of a 60% aqueous acetone solution. Elution is repeated with an additional 5 liter portion of a 60% aqueous acetone solution, and acetone is distilled off from the combined eluate in vacuum. 3 liters of an aqueous solution are obtained, containing 3.96 g. of vitamin $B_{12}$ and having a dry substance content of 27.0 g. Accordingly, the specific active ingredient concentration is 14.66%, and the yield of active ingredient related to the active ingredient concentration of the starting fermentation medium amounts to 88%.

Further treatment of the aqueous concentrate is performed as described in Example 1.

Example 3

10 liters of the fermentation broth according to Example 1 are passed through a floating bed adsorption column containing 200 ml. of Amberlite XAD 7 resin. The pH of the fluid leaving the column is adjusted to 3 to 3.5 with hydrochloric acid, 2 ml. of a 1% KCN solution are added, and the temperature is kept at 80° C. for 10 minutes. The fermentation broth is then cooled to 20° to 30° C. and passed through a column filled with 200 ml. of Amberlite ER 180 adsorption resin. The liquor leaving the column is discharged, and the resin is washed with water, then with a dilute potassium hydroxide solution (pH 10), and finally again with water till neutral. The active ingredient is eluted from the resin with 2 liters of a 70% aqueous methanol solution. Methanol is eliminated from the eluate by evaporation in vacuum. 500 ml. of an aqueous solution is obtained as a residue, which contains 216 mg. of vitamin $B_{12}$ and 1.2 g. of dry substance. The active ingredient concentration related to dry substance is 18%, and the yield related to the active ingredient concentration of the starting fermentation medium amounts to 83%. The concentrate obtained can be used as a fodder additive or can be used for the preparation of crystalline vitamin $B_{12}$ as described in Example 1.

Example 4

10 liter of a fermentation broth obtained by septic aerobic fermentation carried out by inoculation with a sludge are passed through two subsequent adsorption columns, filled with 100 ml. of Amberlite XAD 7 and 100 ml. of Amberlite ER 180, respectively. The disruption of cells and further treatment of the obtained pre-purified fermentation medium are carried out essentially following the procedure described in Example 3. The aqueous solution obtained by evaporation of the eluate contains 202 mg. of vitamin $B_{12}$ and 900 mg. of dry substance. The specific active ingredient concentration is 22.4%, and the yield related to the vitamin $B_{12}$ content of the starting fermentation medium amounts to 77.7%.

Example 5

1 $m.^3$ of a fermentation broth obtained by anaerobic fermentation with a mixed microorganism population derived from sludge, which contain 25 mg./liter of vitamin $B_{12}$ and has a relative viscosity with respect to water of 1.5, are passed through three subsequent columns, each filled with 10 liters of DIAION HP 21 adsorption resin, at a rate of 200 liters/hour. The liquor discharged from the third column has a light color, has no unpleasant odor and its relative viscosity is 1.1. From the pre-purified fermentation broth the biomass is separated, and the concentrate is spray dried, 9.5 kg. of a dry product are obtained, containing 22.5 g. of vitamin $B_{12}$ and having a specific activity of 2370 mg./kg.

Example 6

The aqueous concentrate prepared in Example 1 is used for the preparation of therapeutically applicable crystalline vitamin $B_{12}$ as follows:

To 10 liters of an aqueous concentrate containing 45.2 g. of vitamin $B_{12}$ and 7.3 g. of factor III and having a dry substance content of 331 g. 200 ml. of liquid phenol are added, and the mixture is extracted with 2 liters of a 1:6 mixture of phenol and chloroform. The organic phase is separated and the aqueous phase is repeatedly extracted with 1 liter of a 1:6 mixture of phenol and chloroform. The separated organic phases are combined and washed with 1.5 liter of water, containing 2% of phenol. The aqueous washing liquor is combined with the aqueous phase obtained after the extraction with the 1:6 phenol/chloroform mixture.

To the phenol/chloroform solution containing vitamin $B_{12}$ equal volume, i.e. 3 liter of acetone and 1500 ml. of water are added to bring vitamin $B_{12}$ into the aqueous phase. The aqueous phase is separated and the organic phase is extracted with two 200-ml. portions of water. From the combined aqueous solution the phenol traces are extracted with 1 liter of chloroform. 2100 ml. of an aqueous solution containing 21.7 g. (48% of theoretical yield) of vitamin $B_{12}$ are obtained. According to paper chromatography the product contains only traces (below 1%) of other cobalamine factors. The aqueous solution is concentrated in vacuum to about 500 ml. and is then crystallized from 3000 ml. of acetone in a known manner. 18.1 g. of crystalline vitamin $B_{12}$ are obtained, containing 90.0% of cyanocobalamine.

Acetone is evaporated from the mother liquor of crystallization, the aqueous residue is combined with the aqueous phase obtained after the extraction with a 1:6 mixture of phenol and chloroform and with the aqueous washing liquor of the phenol/chloroform mixture are combined. The 12-liters mixture obtained is washed phenol-free with two 20% by vol. portions of chloroform, whereupon it is evaporated and spray dried. The secondary product obtained contains 24.4 g. of vitamin $B_{12}$ and 6.5 g. of factor III. This product is a "feed grade" vitamin $B_{12}$.

We claim:

1. A process for the treatment of a fermentation broth containing Vitamin $B_{12}$ to prepare a vitamin $B_{12}$ concentrate, which comprises the steps of:
   (a) purifying a fermentation broth containing Vitamin $B_{12}$ within intact microorganism cells by contacting the fermentation broth with a nonionic, macroreticular adsorption resin having a pore size of $10^{-8}$ to $10^{-7}$ m, a grain diameter of at least $10^{-4}$ m, and a specific surface area of at least 200 $m^2/g$ so that the macroreticular adsorption resin adsorbs fermentation broth additives and metabolites of fermentation, whereas the intact microorganism cells containing the Vitamin $B_{12}$ remain in solution;
   (b) disrupting the cells in the fermentation broth purified during the step (a) so that the Vitamin $B_{12}$ is released into solution while debris of the disrupted cells remain suspended in the fermentation broth;
   (c) purifying the fermentation broth treated according to step (b) by contacting the fermentation broth with a nonionic adsorption resin having a pore size of $10^{-8}$ to $10^{-7}$ m, a grain size of at least $10^{-4}$ m, and a specific surface area of at least 200 $m^2/g$, directly without elimination of the cell debris, so that the Vitamin $B_{12}$ is adsorbed on the nonionic adsorption resin; and
   (d) eluting the Vitamin $B_{12}$ from the nonionic adsorption resin with an organic solvent to provide a concentrated Vitamin $B_{12}$ eluate.

2. The process defined in claim 1 further comprising the step of drying the concentrated $B_{12}$ eluate to yield a fodder additive.

3. The process defined in claim 1 further comprising the steps of drying the concentrated Vitamin $B_{12}$ eluate and purifying the dried Vitamin $B_{12}$ concentrates by ion exchange to yield crystalline Vitamin $B_{12}$.

4. The process defined in claim 1 wherein step (d), the organic solvent is a water-miscible solvent which also contains water.

5. The process defined in claim 1 wherein in steps (a) and (c) the adsorption resins used in the purification processes have the same pore size or surface polarity.

6. The process defined in claim 1 wherein in steps (a) and (c) the adsorption resins used in the purification processes have different pore sizes or surface polarities.

7. The process defined in claim 1, wherein in step (a) the purification is carried out repeatedly with adsorption resins that have the same or different pore sizes or structural polarities.

8. The process defined in claim 1, wherein following step (c), the adsorption resin carrying Vitamin $B_{12}$ is washed either with water or with an ammonium hydroxide or alkali metal hydroxide solution at a pH of 8 to 12 to remove impurities.

9. A process for the treatment of a fermentation broth containing Vitamin $B_{12}$ cell concentrate, which comprises the steps of:

(a) purifying a fermentation broth containing Vitamin $B_{12}$ within intact microorganism cells by contacting the fermentation broth with a nonionic macroreticular adsorption resin having a pore size of $10^{-8}$ to $10^{-7}$ m, a grain diameter of at least $10^{-4}$ m, and a specific surface area of at least 200 m$^2$/g so that the macroreticular adsorption resin adsorbs fermentation broth additives and metabolites of fermentation, whereas the intact cells containing the Vitamin $B_{12}$ remain in the fermentation broth;

(b) separating the fermentation broth from the intact microorganism cells containing the Vitamin $B_{12}$; and (c) drying the intact microorganism cells containing the Vitamin $B_{12}$ to yield a Vitamin $B_{12}$ concentrate suitable as a fodder additive.

10. The process defined in claim 9, wherein in step (a) the purification is carried out repeatedly with adsorption resins that have the same or different pore sizes or structural polarities.

* * * * *